United States Patent [19]

Palm et al.

[11] Patent Number: 4,912,236
[45] Date of Patent: Mar. 27, 1990

[54] PURIFICATION OF TETRAHYDROFURAN BY DISTILLATION

[75] Inventors: Christof Palm, Ludwigshafen; Otto H. Huchler, Limburgerhof; Ulrich-Dieter Pessel, Heidelberg; Erdmann Hollborn, Ludwigshafen; Dieter Schmitt, Weisenheim, all of Fed. Rep. of Germany

[73] Assignee: BASF Aktiengesellschaft, Ludwigshafen, Fed. Rep. of Germany

[21] Appl. No.: 231,277

[22] Filed: Aug. 12, 1988

[30] Foreign Application Priority Data

Aug. 12, 1987 [DE] Fed. Rep. of Germany ....... 3726805

[51] Int. Cl.$^4$ ............................................. C07D 307/08
[52] U.S. Cl. ..................................... 549/429; 549/509
[58] Field of Search ................................. 549/429, 509

[56] References Cited

U.S. PATENT DOCUMENTS 4,093,633  6/1978  Tanabe et al. ...................... 549/509
4,332,645  6/1982  Müller et al. .................... 549/429 X

FOREIGN PATENT DOCUMENTS 2509968  3/1977  Fed. Rep. of Germany.
2930144  10/1985  Fed. Rep. of Germany.

Primary Examiner—Richard L. Raymond
Attorney, Agent, or Firm—Keil & Weinkauf

[57] ABSTRACT

Crude water-containing tetrahydrofuran is purified by distillation by a process in which the crude tetrahydrofuran is passed through three distillation columns, water being removed from the bottom of the first column, water-containing tetrahydrofuran being recycled from the top of the second column into the first column, the top product of the third column being recycled to the first column, a distillate being removed at the top of the first column, and pure tetrahydrofuran being distilled off from the bottom product of the second column, in the third column, and the pure tetrahydrofuran being removed from the side take-off of the third column.

4 Claims, 1 Drawing Sheet

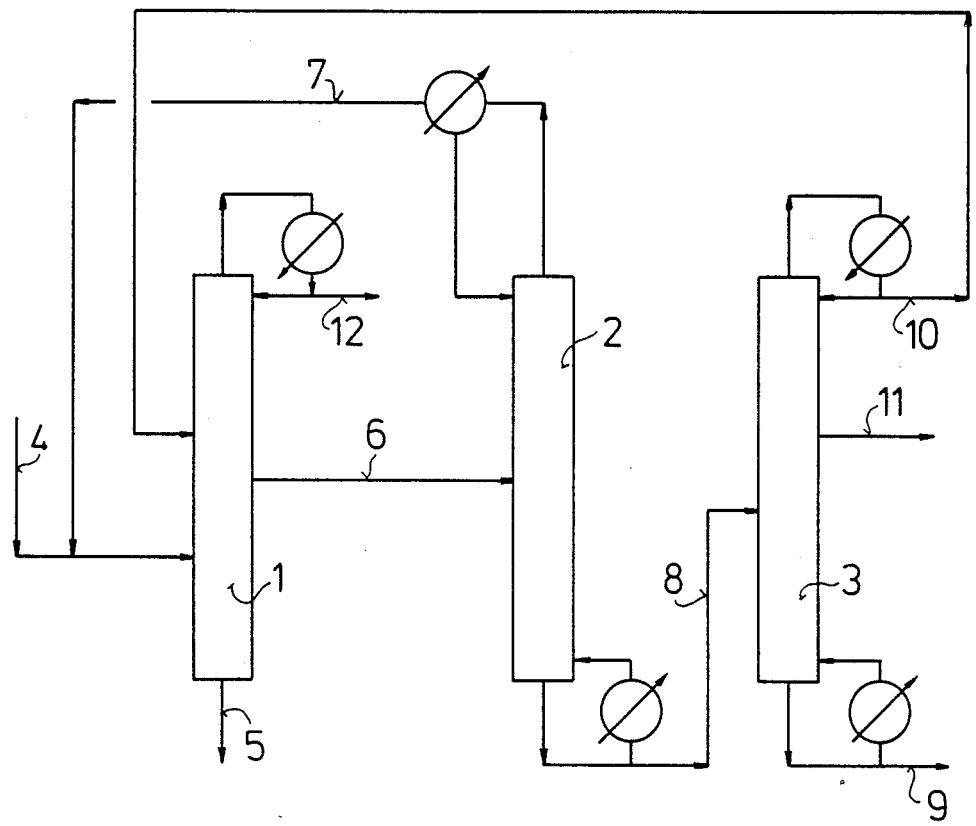

PURIFICATION OF TETRAHYDROFURAN BY DISTILLATION

The present invention relates to a continuous process for the purification of tetrahydrofuran (THM) by distillation.

The preparation of THF by dehydration of butane-1,4-diol over acidic catalysts is described, for example, in German Published Appliation DAS 2,509,968 and German Patent 2,930,144. In the reaction, which takes place according to the equation:

$$C_4H_8(OH)_2 \rightarrow C_4H_8O + H_2O$$

the butane-1,4-diol is cleaved to give 1 mole of THF and 1 mole of water.

The THF formed in the reaction and the water also formed in an equimolar amount and accounting for 20% by weight of the mixture are usually distilled off from the reaction mixture and, in order to remove the water, are fractionated in a column to give the THF azeotrope having a relatively low water content and the waste fraction. The THF azeotrope is then further dewatered by various methods and the THF is purified by distillation.

In a process described in U.S. Pat. No. 4,093,633, pure THF is obtained from the crude water-containing THF by distillative working up in three distillation columns connected in series. In this procedure, the water is removed from the bottom of the first column, which has from 5 to 30 theoretical plates and is operated with a reflux ratio of from 0.5 to 5. The distillate, which still contains water and is passed from the top of the first column into the side of the second column, is separated by distillation in the second column (which has from 5 to 30 theoretical plates and is operated under a pressure of from 3 to 20 kg/cm$^3$ and with a reflux ratio of from 0.5 to 5) in such a way that water-containing THF is recycled from the top of the column into the first column and the essentially anhydrous bottom product is purified by distillation in the third column. The third column has from 10 to 30 theoretical plates and is operated with a reflux ratio of from 0.5 to 2.

The anhydrous THF thus obtained is sufficiently pure for wide range of intended uses. However, it has been found that the polytetrahydrofuran (PTHF) prepared using the THF does not meet the higher requirements set with respect to the color number of PTHF.

It is an object of the present invention to provide a process which makes it possible to obtain a THF having the required high purity from the water-containing crude product obtained in the THF synthesis. We have found that the inadequate purity of the THF distilled by the known methods is due to lower boiling impurities which remain in the THF and which have to be reliably removed from THF. This cannot be satisfactorily achieved by a further distillation. In addition, a very large number of theoretical plates an very high reflux ratios are required, and a large amount of THF is lost with the low boiling impurities removed at the top in the purification column.

We have found that this object is achieved and that a THF having the required high purity is obtained in the purification of crude water-containing THF by distillation, in which the crude tetrahydrofuran is passed through three distillation columns, water being removed from the bottom of the first column, water-containing tetrahydrofuran being recycled from the top of the second column into the first column and pure tetrahydrofuran being distilled off from the bottom product of the second column, in the third column, if a side stream of the first column is passed into the second column, the top product of the third column is recycled to the first column, distillate is removed at the top of the first column and the pure tetrahydrofuran is obtained from the side take-off of the third column.

The novel process makes it possible to obtain a very pure THF, the number of theoretical plates being smaller and the reflux ratio no higher in comparison with the most familiar inadequate methods, for the selective reliable removal of low boilers.

In the novel process, purification of the crude water-containing THF by distillation is carried out in three distillation columns connected in series by a procedure as illustrated, for example, in the Figure. The columns are operated in a conventional manner, the first column (1) with from 30 to 50 theoretical plates and under atmospheric pressure and with a reflux ratio of from 1.5 to 2, based on the side stream (6), the second column (2) with from 10 to 30 theoretical plates and under from 4 to 20 bar and with a reflux ratio of from 1 to 2, and the third column (3) with from 40 to 50 theoretical plates and under atmospheric pressure and with a reflux ratio of from 4 to 8, based on the side stream.

The crude water-containing THF has a water content of from 18 to 28% by weight an contains, for example, up to 5% by weight of impurities due to the raw materials used in the THF synthesis, eg. 2,3-dihydrofuran and 2-and 3-methyltetrahydrofuran. The said THF is passed into the side of the first column. The feed line (4) is advantageously located in the lower half, above the bottom of the column. Water is removed (5) from the bottom of the column. The column (1) has a side take-off (6) mounted above the feed line (4), through which take-off a liquid THF/water mixture is removed and passed into the side of the pressurized column (2), with an increase in pressure. From the top of this pressurized column, water-containing THF is recycled (7) into the first column. The bottom product of the second column, which is essentially anhydrous, is passed into the side of the third column (8). High boiling impurities are removed (9) from the bottom of the third column.

According to the invention, the top product of the third column, which still contains residues of water and low boilers (10), is also recycled into the first column, while the very pure THF is removed from the side take-off of the third column (11). It is also essential to the invention that a distillate is removed (12) at the top of the first column, the said distillate evidently containing the byproducts which are responsible for reducing the quality of the pure THF and which remain in the product in the familiar working up of THF by distillation. In the process of this invention, the first column is preferably operated in such a way that a distillate in which the THF content has increased to 50-10, preferably 30-10, % by weight is rectified at the top of the column. This distillate is removed from the circulation and is, for example, burned.

In the Example, parts are by weight.

EXAMPLE

The distillation apparatus shown in the Figure was used. It consists of three columns (1), (2) and (3), of which column (1) has 40 theoretical plates and column (3) has 46 theoretical plates, the columns being operated under atmospheric pressure. Column (2) is operated under superatmospheric pressure of 5 bar and has 30 theoretical plates. A vapor mixture of 80% by weight of THF and 20% by weight of water, which contained 0.1% of 2,3-dihydrofuran as a typical low boiling impurity and 0.5% of 2- and 3-methyltetrahydrofuran as typical high boiling impurities was passed into column (1) via feed line (4). At the same time, the vapor top product of column (2) was fed via line (7) to column (1), and the liquid top product of column (3) was fed via line (10) to column (1). Column (1) was operated with a side take-off (6), a top take-off (12) and a bottom take-off (5). The reflux ratio was about 1.7, based on the side take-off. Water was discharged from the bottom take-off (5)

A water-containing THF which had a water content of from 5 to 6% and still contained 40% of the original content of dihydrofuran and all of the methyltetrahydrofurans was removed from column (1) as a side stream (6).

A little more than 0.1% of the feed was removed as top product (12). The top product had a THF concentration of 20% and a dihydrofuran concentration of about 70% and contained more than 80-90% of the dihydrofuran and low boiling impurities fed in.

The side stream (6) of the first column was fed into the second column (2) with an increase in pressure, column (2) being operated under 5 bar and with a reflux ratio of about 1. The top product (7) of the second column contained virtually all the water and remain in low boilers and was recycled to the first column (1). The bottom product, which proved to be virtually anhydrous and still contained about 40 ppm of dihydrofuran was passed into the third column (3).

The third column, ie. purification column, was operated with a reflux ratio of about 5, based on the side stream. The very pure THF removed from the side take-off (11) had a purity of 99.99% and contained less than 30 ppm of dihydrofuran and 40 ppm of methyltetrahydrofuran.

From 1 to 2% of the THF feed was removed as top product from the third column (3) and recycled to the first column (1). It contained 200 ppm of dihydrofuran. From 0.6 to 0.7% of the feed (8) was removed as bottom product (9). The bottom product contained virtually all the methyletrahydrofuran, in 80% concentration.

We claim:

1. A process for the purification by distillation of crude water-containing tetrahydrofuran obtained by the dehydration of butane-1,4-diol over an acidic catalyst, in which the crude tetrahydrofuran is passed through three distillation columns, water being removed from the bottom of the first column, water-containing tetrahydrofuran being recycled from the top of the second column into the first column and pure tetrahydrofuran being distilled off from the bottom product of the second column in the third column, wherein a side stream of the first column is passed into the second column, the top product of the third column is recycled to the first column, a distillate is removed at the top of the first column, and the pure tetrahydrofuran is obtained from the side take-off of the third column.

2. The process of claim 1, wherein a distillate which contains not more than 50% by weight of tetrahydrofuran is removed at the top of the first column.

3. The process of claim 1, wherein the distillate removed at the top of the first column contains from 10 to 30% by weight of tetrahydrofuran.

4. The process of claim 3, wherein the distillate removed from the top of column 1 contained a dihydrofuran concentration of about 70% and contained more than 80% of the dihydrofuran and low boiling impurities contained in the crude tetrahydrofuran.

* * * * *